United States Patent [19]

Montanari

[11] 4,222,970
[45] Sep. 16, 1980

[54] PROCESS FOR PRODUCING PHOSPHONOMYCIN

[76] Inventor: Roberto Montanari, viale Bianca Maria, 9 Milan, Italy

[21] Appl. No.: 916,145

[22] Filed: Jun. 16, 1978

Related U.S. Application Data

[63] Continuation-in-part of Ser. No. 811,841, Jun. 28, 1977, abandoned.

[30] Foreign Application Priority Data

Aug. 4, 1976 [IT] Italy ............................. 26005 A/76

[51] Int. Cl.$^2$ .............................................. C07F 9/40
[52] U.S. Cl. ............................. 260/968; 260/348.31; 260/348.42
[58] Field of Search ..................... 260/348.42, 348.31, 260/983, 956, 968

[56] References Cited

U.S. PATENT DOCUMENTS

| | | | |
|---|---|---|---|
| 3,188,309 | 6/1965 | Mukalyama et al. | 260/957 |
| 3,597,451 | 8/1971 | Firestone | 260/348 |
| 3,849,482 | 11/1974 | Christensen et al. | 260/501.21 |

OTHER PUBLICATIONS

E. J. Glamkowski et al., J. Org. Chem., vol. 35, No. 10 (1970) 3510–3512.
Chemical Abstracts, vol. 58 (1963) 1322b.

Primary Examiner—Norma S. Milestone
Attorney, Agent, or Firm—McGlew and Tuttle

[57] ABSTRACT

A novel synthesis of the antibiotic phosphonomycin provided which avoids formation of butylphosphochloridite and instead obtains the intermediate butylpropinyl-phosphite by the mixed anhydrides method. Simplified reaction apparatus is used. Very high yields of a further intermediate, di-t-butylpropadienylphosphate are obtained using the mixed anhydrides process starting with dibutylphosphite. The synthesis of phosphomycin is carried further by hydrogenation of the di-t-butylpropadienylphosphonate using hydrazine hydrate and Ni-Raney with excellent yields to give the second intermediate di-t-butyl-cis-1,2-propenylphosphonate which is in turn converted to the desired phosphomycin by converting to the free phosphonic acid e.g., by reflux with strong acid to remove the t-butoxy groups, followed by epoxidation of the resultant phosphonic acid with hydrogen peroxide and sodium tungstate to yield cis-1,2-epoxypropylphosphonic acid. Optical resolution is then carried out by selective crystallization with (+)-α-phenylethylamine and recrystallization.

1 Claim, No Drawings under the numbers 4,222,970

PROCESS FOR PRODUCING PHOSPHONOMYCIN

CROSS REFERENCE TO COPENDING APPLICATION

This application is a continuation-in-part of our copending application Ser. No. 811,841, filed June 28, 1977, now abandoned, by Roberto Montanari for "A PROCESS FOR PRODUCING PHOSPHOMYCIN".

BACKGROUND OF THE INVENTION

1. Field of the Invention

The present invention relates to a novel industrial process for the production of the antibiotic Phosphonomycin.

Phosphonomycin is L-(cis)-1,2-epoxypropyl-phosphonic acid and has the following structure (I):

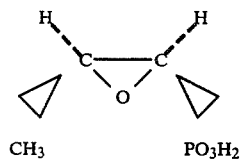

Phosphonomycin is a new antibiotic which was discovered in Spain in 1966. It was found for the first time in a fermentation broth of a strain of *Streptomyces fradiae*, isolated in the province of Alicante. Later there were found other strains of *S. Virichromogenes* and of *S. Wedmorensis* which also produced phosphomycin [*Science*, 166, 122–3, (1967)].

2. Prior Art

The biological and chemico-physical characteristics of (I) have been described by E. J. Glamkowski et al in *J. Org. Chem.*, 35, 3510 (1970):

"Its bactericidal mode of action is via irreversible binding to the enzyme pyruvate-uridine diphospho-N-acetylglucosamine, thereby inhibiting cell wall synthesis.

Phosphonomycin has been shown to be (−)-(1R,2S)-1,2-epoxypropylphosphonic acid. Proof of structure was obtained by synthesis together with a chemical determination of the absolute configuration."

Phosphonomycin has been prepared also synthetically (G. B. Christensen et al, *Science*, loc. Cit.; E. J. Glamkowski, *J. Org. Chem.*, loc. cit.)

Essentially, this method of synthesis previously reported in the literature takes place through the following steps:

(1) Preparation of the t-butyl-phosphochlor idite or phosphochloridite, t-(BuO)$_2$PCl;
(2) Reaction of the latter with propargyl alcohol to obtain the t-butyl-propynyl-phosphite;
(3) Isomerisation of the latter to the (allenic) propadienylphosphonate;
(4) Hydrogenating same to the cis-propenylphosphonate;
(5) Hydrolysis to obtain the cis-propenylphosphonic acid;
(6) Epoxidation and optical resolution to obtain the L isomer of the desired phosphonomycin.

DESCRIPTION OF THE INVENTION

The inventor has now realized that it is possible to simplify this method of synthesis of the prior art in a manner completely unexpected, as to obtain a racemic product, with excellent yields, making two unexpected changes in the procedure described in the literature. The purity of the final product depends on the effective separation of the antipodes.

A first feature, according to the present invention, consists of avoiding the formation of the butylphosphochloridite and of obtaining the butyl-propynyl-phosphite by the mixed anhydrides method. This operation makes it possible to avoid using phosphorous trichloride, with the subsequent simplification of the reaction apparatus, and to obtain extremely high yields of the desired compound. The dibutylphosphite used as starting material is readily available commercially.

Applying to said compound the mixed anhydrides process described by G. P. Schiemenz and H. Engelhand (*Chem. Berg.* 92, 857) and treating the anhydride thus obtained with propargylic alcohol one obtains directly the di-t-butyl-propadienylphosphonate described by J. Glamkowski et al in *J. Org. Chem.* 35, 3510 (1970).

The most obvious advantage of utilizing the mixed anhydride method rather than using the chloro derivatives is the almost quantitative yield obtained, based on the dibutylphosphite used. The reaction is carried out at room temperature up to the time when the propargylic alcohol is added and the reaction mixture is then heated to 40° C. On the other hand, if the chloro derivative is used, the first phase of the reaction must be carried out at a low temperature, and this is an undesirable factor in an industrial operation.

The second feature according to the invention resides in the fact that the hydrogenation of the propadienylphosphonate to the propenylphosphonate takes place using hydrazine hydrate, and Ni-Raney, with excellent yields, rather than with H$_2$ and Pd. The advantage of this step is the fact that hydrogen is not used, that a reduction apparatus which has to operate under reduced pressure is not necessary and that a catalyst much less expensive is used.

EXAMPLE 1

Preparation of di-t-butyl-propadienylphosphonate 0.5 mols of di-t-butylphosphite in 700 ml of anhydrous benzene are reacted at a temperature between 10° C. and 25° C., with one mol of triethylamine and then, slowly, with one mole of ethyl chloroformate. The reaction mixture is filtered and the solid triethylamine hydrochloride is removed from the reaction mixture. To the filtrate there is added one mol of propargylic alcohol and the mixture is heated to 40°–50° C. for 30 minutes. There is then isolated therefrom, by conventional means, the product which is in a pure state and in quantitative yields.

In Example 1, the initial ester product is thought to be the propargyl di-t-butyl phosphite, which isomerises under the action of gentle heat to the di-t-butyl 1,2-propadienylphosphonate.

EXAMPLE 2

Preparation of di-t-butyl-cis-1,2-propenylphosphonate

To a benzene solution of 700 ml containing 0.5 mols of the compound prepared in Example 1, there is added a 50—50 water-ethanol solution (50 ml) containing 0.5 mols of hydrazine hydrate and 0.1 g of Ni-Raney. The mixture is stirred at room temperature for one hour and the solid catalyst contained therein removed by filtration. By removal of the solvent under reduced pressure there is obtained, in yields higher than 90%, the desired di-t-butyl-cis-1,2-propenylphosphonate having the characteristics described in *J. Org. Chem.*, 35, 3511 (1970).

EXAMPLE 3

Preparation of Phosphonomycin

The di-t-butyl cis-1,2-propenylphosphonate obtained in Example 2 is suitably converted to phosphonomycin by reflux with strong acid, such as hydrochloric acid, to produce the free phosphonic acid by removal of the t-butoxy groups, followed by epoxidation of this acid in the presence of hydrogen peroxide and sodium tungstate to produce the cis-1,2-epoxypropylphosphonic acid. Optical resolution is then carried out by selective crystallisation with (+)-α-phenylethylamine and recrystallisation; if desired: the optically active base is present in the reaction mixture during the epoxidation to give a precipitate of partly or wholly resolved salt out of the epoxidation reaction mixture.

Further, if convenient, the benzene solution from the reaction according to Example 2 containing di-t-butyl-cis-1,2-propenylphosphonate, is heated to reflux with a few parts of the free phosphonic acid added as catalyst and carrying on the reaction by removal of the isobutylene gas evolved and distillation off of benzene during the process. The crude product is then used directly in the next step of the phosphonomycin synthesis after first removing all traces of benzene in vacuo.

The crude cis-propenylphosphonic acid is an oil, and this intermediate is epoxidized to cis-1,2-epoxypropylphosphonic acid which is a racemic mixture and is then selectively crystallized with (+)α-phenylethylamine to yield the desired L-cis-1,2-epoxypropylphosphonic acid, or phosphonomycin.

The cis-propenylphosphonic acid is dissolved (1 mol) is propanol (800 parts/vol.) and 0.67 mole of (+)α-phenylethylamine is added, after which 0.55 mol triethylamine is added to the resultant mixture until a pH of about 5.8–5.9 is reached. The resultant warm solution is treated in one portion with 0.015 mol of sodium tungstate dihydrate and about 1/5 parts by weight of ethylene diamine tetra acetic acid dissolved in about 15 parts/vol. of warm water. To the resultant solution is added slowly 1.53 mol of hydrogen peroxide (30% aqueous solution) for about 15 minutes with stirring. The temperature is maintained at from 40° to 55° C. After reaction is completed the temperature of the reaction solution is kept at 50°–55° C. for an hour to complete the epoxidation. Then the solution is cooled to −5° C. for a period of 30 min. to initiate crystallization. After stirring for 2 hours at −5° C., the L-cis-1,2-epoxypropenylphosphonate is filtered and the cake washed with cold propanol. Resolution is completed by dissolving the dried salt in hot (75°–80° C.) propanol and treating the resultant solution with charcoal and filtering while hot through a preheated filter device. To the hot filtrate is added warm (60°–70° C.) water. Crystallization of the monohydrate commences within a few minutes. After stirring the resultant mixture at 0° C. for 2 hours, the product is filtered, washed with cold propanol and dried in vacuo at 45° C. The so-obtained product is the salt of phosphonomycin with (+)-α-phenylethylamine i.e. (+)- -phenylethylammonium L-cis-1,2-epoxypropylphosphonate.

What is claimed is:

1. Process for the production of di-t-butyl cis-1,2-propenyl phosphonate which comprises in combination the steps of:
   (a) reacting di-t-butylphosphite with triethylamine and ethyl chloroformate to form a mixture of solid triethylamine hydrochloride and liquid solution;
   (b) removing the solid triethylamine hydrochloride of step (a) from the liquid solution by filtration;
   (c) adding propargylic alcohol to the liquid solution from step (b) and heating gently the resultant mixture at about 40°–50° for about one-half hour thereby obtaining di-t-butyl 1,2-propadienyl phosphonate;
   (d) treating the di-t-butyl 1,2-propadienyl phosphonate from step (c) by reduction with an aqueous-ethanolic solution containing hydrazine hydrate and Ni-Raney catalyst to form a reaction mixture, and stirring the reaction mixture at room temperature;
   (e) removing the solid Ni-Raney catalyst by filtration after stirring the mixture resultant from step (d) and separating the filtrate as a liquid product; and
   (f) recovering the desired aforesaid intermediate composition from the liquid product of step (e) by distillation while removing liquid solvent under reduced pressure, whereby the desired di-t-butyl cis-1,2-propenylphosphonate is obtained.

* * * * *